(12) United States Patent
Hartung

(10) Patent No.: US 6,932,599 B1
(45) Date of Patent: Aug. 23, 2005

(54) IRRADIATION UNIT

(75) Inventor: Martin Hartung, Munich (DE)

(73) Assignee: 3M ESPE AG, Seefeld (DE)

( * ) Notice: Subject to any disclaimer, the term of this patent is extended or adjusted under 35 U.S.C. 154(b) by 65 days.

(21) Appl. No.: 10/070,642

(22) PCT Filed: Aug. 18, 2000

(86) PCT No.: PCT/EP00/08058

§ 371 (c)(1),
(2), (4) Date: Mar. 11, 2002

(87) PCT Pub. No.: WO01/19280

PCT Pub. Date: Mar. 22, 2001

(30) Foreign Application Priority Data

Sep. 10, 1999 (DE) .............................. 199 43 393

(51) Int. Cl.[7] .............................................. A61C 3/00
(52) U.S. Cl. ...................... 433/29; 362/800; 362/804
(58) Field of Search ...................... 433/29, 215; 606/1, 606/13, 16; 607/88; 362/119, 800, 804

(56) References Cited

U.S. PATENT DOCUMENTS

| 5,420,768 | A | | 5/1995 | Kennedy |
| 5,549,660 | A | | 8/1996 | Mendes et al. |
| 5,634,711 | A | * | 6/1997 | Kennedy et al. ............ 362/119 |
| 6,102,696 | A | * | 8/2000 | Osterwalder et al. ......... 433/29 |
| 6,200,134 | B1 | * | 3/2001 | Kovac et al. ................. 433/29 |
| 6,331,111 | B1 | * | 12/2001 | Cao ............................. 433/29 |
| 6,692,251 | B1 | | 2/2004 | Logan et al. |
| 6,719,559 | B2 | * | 4/2004 | Cao ............................. 433/29 |
| 2001/0019446 | A1 | | 9/2001 | Hartung |
| 2004/0029069 | A1 | | 2/2004 | Gill et al. |

FOREIGN PATENT DOCUMENTS

| DE | 0755662 | | 1/1997 |
| DE | 19619154 | | 6/1997 |
| DE | 19619155 | | 6/1997 |
| DE | 0879582 | | 11/1998 |
| DE | 19721311 | | 12/1998 |
| DE | 10006286 C1 | | 10/2001 |
| EP | 0880945 | | 12/1998 |
| EP | 1 138 276 | * | 10/2001 |
| JP | 8141001 | | 6/1996 |
| JP | 9010238 | | 1/1997 |
| WO | 95/07731 | | 3/1995 |
| WO | 97/36552 | | 10/1997 |
| WO | 9736552 | | 10/1997 |

(Continued)

OTHER PUBLICATIONS

International Search Report.

(Continued)

Primary Examiner—Ralph A. Lewis
(74) Attorney, Agent, or Firm—Crowell & Moring LLP

(57) ABSTRACT

The radiation device has an array (11) of light-emitting diodes (12) providing light beams which are directed onto a focus region (20) at the input end of a light conductor (18), used for directing a focused light beam onto the radiation point. The light-emitting diodes are supported in a planar holder (19) at different inclination angles, for providing a light cone illuminating the light conductor input end from their output beams.

21 Claims, 1 Drawing Sheet

| | FOREIGN PATENT DOCUMENTS | |
|---|---|---|
| WO | 99/16136 | 4/1999 |
| WO | 9916136 | 4/1999 |
| WO | 99/35995 | 7/1999 |
| WO | 9935995 | 7/1999 |
| WO | 00/13608 | 3/2000 |
| WO | 0013608 | 3/2000 |

OTHER PUBLICATIONS

International Preliminary Examination Report.

* cited by examiner

IRRADIATION UNIT

FIELD OF INVENTION

The invention relates to an irradiation unit of high light power, comprising a light-emitting unit, preferably LEDs, and a light-guiding unit with a light-absorbing region such as a fiber-optic optical conductor, which is preferably used in the field of medicine.

BACKGROUND OF THE INVENTION

JP-A-9-10238 discloses a dental irradiation unit in which an array of light-emitting diodes is arranged on he hemispherical surface of an optical conductor member, in the shape of a conical sector, made from quartz or plastic, the tip of which merges into a rigid optical fiber rod. The beams of the light-emitting diodes are focused by the optical conductor member by reflection at the conical wall and passed into the rigid optical fiber rod.

WO-97/36552 discloses a further dental irradiation unit in which a planar array of light-emitting diodes with parallel optical axes is situated opposite the curved entrance surface of a likewise conical optical conductor member. This condenser is coupled on the output side to an optical conductor and filled, if appropriate, with an optically transparent liquid.

Apart from the fact that such conical optical conductor members such as have been described in the above publications, or else in WO 99/16136 (FIG. 4), are expensive to produce, and increase the weight of the unit, they also cause substantial radiation losses. These result from the fact that with each reflection of a light beam at the conical wall of the optical conductor member the beam is deflected by double the cone angle from the optical axis. This leads even after a few reflections to the fact that the angle for total reflection in the optical conductor is exceeded and the beams exit from the optical conductor or, in the case of silvering of the optical conductor, the beams even are reversed in direction and are therefore guided back not to the light exit orifice but to the light entrance orifice. Such arrangements therefore function only for a fraction of the light irradiated by the LEDs whose beams are tilted relative to the optical axis only in a very narrow angular range. Consequently, the predominant portion of the light emitted by the LEDs cannot be used to illuminate the treatment surface, since the luminous cones with the aid of which LEDs emit light usually have usually have substantially larger aperture angles.

Moreover, WO-99/16136 (FIG. 6) discloses a unit with a multiply conical optical conductor member in the case of which a plurality of annular light entrance surfaces are placed in front of a circular light entrance surface. In this case, the multiply conical optical conductor member directs the light from the first circular light entrance surface into the central region between the first annular light entrance surface. Together with the light from the LEDs, which irradiate this light entrance orifice in annularly arranged fashion, it is now conducted into the center of a further combination of an LED ring and annular entrance surface. The light thus collected is now guided to an exit orifice by the optical conductor, which is once again conical in its further course.

For the reasons named above, with this arrangement as well only a small fraction of the beams emitted by the LED reaches the light exit orifice and thus the site to be irradiated. By connecting a plurality of conical optical conductor members in series, the efficiency of the regions situated furthest removed from the exit orifice is reduced once more even by comparison with a singly conical condenser. In addition, the fabrication of the multiply conical optical conductor is, once again, more complicated and more expensive.

There are also other designs of irradiation units based on LED that manage without a conical optical conductor member and the disadvantages associated therewith. Thus, optical positive lenses for concentrating the beams emitted by an LED array and focusing the latter onto the light entrance surface of an optical conductor are proposed in JP 08-141001 (FIG. 1) and WO 99/35995 (FIG. 4). In this case, the totality of the beams emitted by the individual LEDs in the direction of the positive lens in deflected. The deflection in the desired direction and focusing of the beams succeed, however, in turn, only for the fraction of the beams that strike the positive lens in a substantially parallel fashion or, depending on the size of the light entrance surface, deviate slightly from the direction. A substantial fraction of the beams cannot be guided by the positive lens onto the light entrance orifice, and is therefore lost for the irradiation of the treatment site.

In the case of the arrangement shown in FIG. 1 of WO 99/35995, 9 LEDs are aligned individually in the direction of an optical conductor, in which case it was possible to observe only a partial hardening of a light-hardening sample. This is to be ascribed to inadequate light power as a consequence of non-optimum launching of light, as well as of the small number of the LEDs that can be used with the arrangement described.

Another unit described in WO/00/13608 is based on a similar arrangement of the LEDs in relation to the light entrance orifice of an optical conductor. The light power is increased by, on the one hand, making use of a conical optical conductor and, on the other hand, applying an increased working current (multiple times the nominal working current) to the diodes. The conical optical conductor also has the problems already described above. A further disadvantage caused by the high operating currents is that disproportionately high heat occurs at the LEDs, as a result of which the unit becomes hot after a short time, and cannot be used for a prolonged period of time until it has cooled down. In addition, the service life of LEDs suffers under the high operating currents, resulting in a continuous drop in light power over time.

The arrangements for LEDs in the form of individual semiconductor chips on a common substrate, as proposed in WO 99/35995 or EP-A-0 879 582 are also not without their problems. The individual elements heat one another up, resulting in setting limits for the light intensity and/or the service life. In addition, the production of such arrangements is substantially more complicated and expensive, since it is not possible to resort to standard components which can be handled effectively in mechanical terms.

It is therefore common to the above units that the achievable light powers are limited by the arrangements described there for the LEDs.

SUMMARY OF THE INVENTION

Consequently, it is an object of the present invention to provide an irradiation unit with improved light power with the aid of which it is possible, for example, to achieve quicker and more reliable light-induced hardening of dental filling materials which is quicker and more reliable.

This object is achieved by means of an irradiation unit as described hereinbelow in more detail.

The light-emitting unit in the sense of the invention is to be understood as any form of radiation source that generates light, preferably with a wavelength in the range from 400 to 500 nm. This emission is preferably performed in a directed fashion. The light-emitting unit usually comprises a plurality of light-emitting elements.

It includes, in particular, light-emitting diodes (LED). However, it is also possible to use laser diodes as described in European patent application EP-A-0 755 662.

A light-absorbing unit in the sense of the invention is any device capable of absorbing and outputting again in a directed fashion light that is generated by the light-emitting unit or the light-emitting elements.

These are usually what are termed rigid optical fiber rods which comprise a multiplicity of bundled glass fibers. Via a coupling or a thread, these rigid optical fiber rods can be connected reversibly to the light-emitting unit or the housing containing the latter.

Also covered, however, are conventional filter disks, scattered light disks or light wave converters, as described in German patent application DE 100 06 286.5.

The terms "contain" and "cover" in the sense of the invention introduce a non-exhaustive enumeration of features.

The invention is based on the surprising finding that it is possible with good efficiency for the light of an array of light-emitting diodes to be concentrated onto the light entrance orifice of an optical conductor and projected into the latter even without a positive optical system, operating in a reflecting fashion, or positive lenses.

The basis for achieving a high light power in such cases, is the finding that there is a substantially close relationship between the achievable light power and the angle of emission of the light-emitting elements, their distance from the light entrance surface and their alignment relative to one another as well as to the optical conductor. This dependence is related to the fact that it is particularly favorable when the light cones of the light-emitting elements in each case illuminate the light entrance surface of the optical conductor as completely as possible, that is to say the surfaces illuminated by the light cones corresponds substantially to the surface of the entrance orifice. Since the cross section of the entrance orifice is permanently prescribed, the above requirement concerning the aperture angle results in the distance of the light-emitting elements relative to the entrance surface. Were this distance to be enlarged, a portion of the light cone would shine past the optical conductor and thereby not be useful. In the case of a smaller distance relative tot he optical conductor, the number of the light-emitting elements given space on the array would be reduced.

As described in the exemplary embodiments, it is possible when taking account of these dependencies to find arrangements for which the predominant portion of the radiation emitted in light cones by the individual light-emitting elements can be launched into an optical conductor and thus guided to a treatment site, whilst simultaneously as large a number of light-emitting elements as possible can be integrated in the array.

These both contribute to a light power of the irradiation unit that is as high as possible.

Slight differences in the level of illumination such as can come about necessarily because the light-emitting elements, which are arranged more toward the center, generate an approximately circular illumination pattern while, by contrast, the light-emitting elements arranged further at the edge generate more of an elliptical pattern, are unavoidable and have no sizeable practical relevance. More important, however, is that the distance of the central light-emitting elements in the arrangements shown in the figures is dimensioned such that even the elliptical illuminating spots of the elements lying at the edge can still be collected completely and do not shine past the entrance surface.

It is also important in this case that the beams are radiated directly onto the light entrance surface, that is to say the beams do not have their direction deflected by, for example, positive lenses or condenser optical systems operating in a reflecting fashion, since such a deflection is always favorable only for a small fraction of the beams with reference to their ability to be launched into an optical conductor. Beams already having a slightly different direction can, however, no longer be used after the deflection, because they shine past the entrance orifice, or the acceptance angle, the maximum angle at which beams can still be launched into an optical conductor, is exceeded.

Surprisingly, it is possible to use the arrangement of light-emitting elements according to the invention in at least two mutually separated planes even to increase further the light power achievable in the irradiation unit without the need for the presence of light-guiding or light-focusing elements between the planes.

It is also advantageous that owing to this arrangement the irradiation unit can be fashioned to be relatively compact and easy to manipulate without thereby impairing the available light power.

In the case of the arrangement in at least two planes, as well, it is particularly advantageous when the light cones essentially completely illuminate the entrance surface. Since the planes are arranged at a different distance in relation to the entrance orifice, different angles of emission of the light-emitting elements are advantageous in the individual planes.

Light-emitting elements that are arranged in the first plane, lying closest to the entrance orifice, preferably have a larger angle of emission than the remaining light-emitting elements of the downstream plane(s). This is also advantageous, in particular, by virtue of the fact that light-emitting elements with a relatively large angle of emission of, for example, +/−30° (for example Nichia NSPB 310A) emit approximately 70% of their total radiation into the forwardly directed and useful light cone. For light-emitting elements with narrower angles of emission of, for example, +/−15° (for example Nichia NSPB 300A), this portion is only approximately 50%. The remainder of the radiation is emitted laterally and in a way that is not useful. Light emitting elements which are further removed from the optical conductor must, however, emit their light into narrower light cones so that the latter can strike the entrance orifice completely and thus be collected.

It is also advantageous when the distance of the individual planes from the optical conductor and from one another is as small as possible. A distance between the individual planes that corresponds essentially to the overall length of the light-emitting elements used has proved to be favorable.

If appropriate, the light-emitting unit is covered with a transparent disk in order to protect the light-emitting elements against moisture and dirt with the optical conductor removed. It has proved to be particularly advantageous for this cover disk to be designed in the form of a prismatic disk, since it is possible thereby for the light power to be raised once. However, it is a precondition for this that the prismatic disk does not disturb the direct irradiation of the entrance surface of the light-absorbing unit, that is to say does not influence the direction of the light beams directed onto the latter, but also does not have a dimming effect. The latter can easily be achieved by an optical coating.

A prismatic disk in the sense of the invention is a transparent device in the form of a relatively flat conical frustum with a flat top side and an under side of smaller diameter, the diameter of he under side corresponding essentially to the diameter of the light-absorbing unit.

The prismatic disk has two regions that behave differently in optical terms, a flat cylindrical region and a rotationally symmetrical prismatic edge region. The prismatic disk has no uniform focal point and functions predominantly according to aspects of refraction and not of reflection.

The cylindrical unit does not deflect light beams that strike at right angles, and deflects obliquely striking light beams in accordance with Snellius' law of refraction, only a slight parallel displacement resulting between the entering and exiting beams. The direction of the beams remains substantially unchanged, however.

The function of the prismatic edge region consists in deflecting in a directed fashion onto the entrance orifice light that would be shone past the side of the entrance orifice by the light-emitting elements situated closest to the entrance orifice despite an optimized arrangement.

By fitting such a prismatic disks, the entrance orifice is optically enlarged in its diameter, as well, without there being an appreciable disturbance of the beam path in the central region.

The prismatic disk can be oriented both with the under side and with the top side parallel to the light-absorbing unit.

It is also conceivable for two prismatic disks to lie one on another, giving rise to a structure in the shape of a discus.

The prismatic disk can be produced from glass or transparent plastic. The material preferably has a refractive index in the range from 1.4 to 1.6.

The prismatic disk is preferably arranged parallel to the entrance orifice of the light-absorbing element at a distance corresponding to its thickness or height. The space between the prismatic disk and entrance orifice is usually filled with air.

The light-emitting elements are preferably mounted on only one, usually flat circuit board in order to save production costs. Individual, mutually separated planes can be produced by a different length of the connecting wires for the light-emitting elements.

The problem of dissipating the heat generated by the light-emitting elements during operation of the irradiation unit can be solved by using a circuit board coated on both sides. For this purpose, the cathodes generating the heat loss are fitted on the under side, and the anodes on the top side. Since a heat sink, for example in the form of a copper member or aluminum member, is usually located on the under side of the circuit board, heat transfer is improved.

The irradiation unit usually also has an electronic control unit for controlling voltage and current intensity for the light-emitting elements, a storage unit for electric energy such as batteries or accumulators, preferably lithium ion, NIMH or Ni/Cd accumulators, a display unit and a housing.

The housing is preferably configured in such a way that it essentially a surface without gaps into which the display unit is integrated.

Preferred exemplary embodiments are explained below with the aid of he drawings, in which:

DETAILED DESCRIPTION OF THE INVENTION

Figure 1:
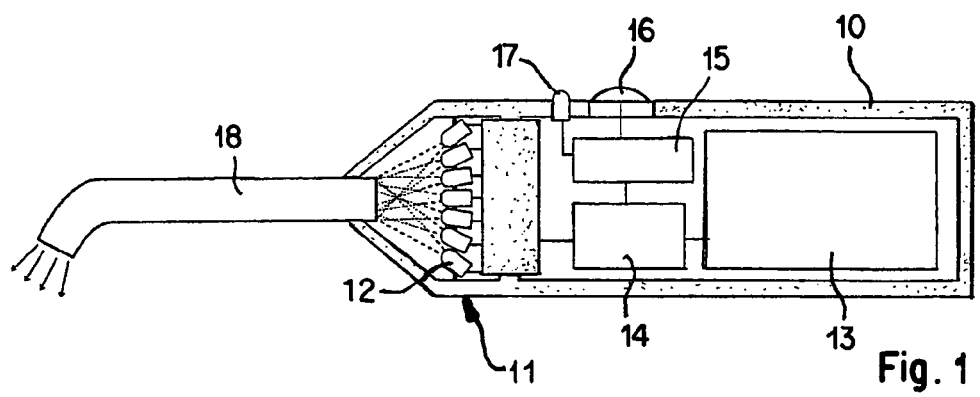
FIG. 1 shows a longitudinal section through the irradiation unit.
Figure 2:
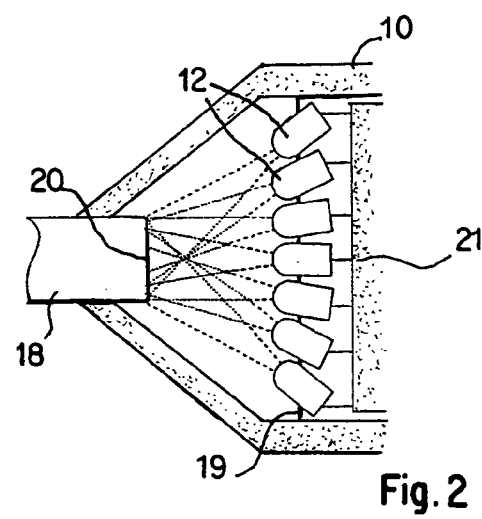
FIG. 2 shows an enlarged illustration of the front part of the unit according to FIG. 1.

The hand-held unit, shown in FIG. 1, for irradiating dental plastics includes in the front region of a substantially cylindrical housing (10) a light-emitting unit (11) in the form of an array, for example, fifty, individual light-emitting elements (12), such as light-emitting diodes, which can also be laser diodes.

The light-emitting elements (12) are fed from a battery (13), arranged in the rear part of the housing (10), via a driver stage (14) that is time-controlled by a control circuit (15). The control circuit (15) is connected to a closing push-button (16) arranged on the side of he housing (10), and to a display diode (17) likewise arranged on the side of the housing (10). Projecting from the front conical end of the housing (10) is a light-conducting unit (18) in the form of an optical fiber rod curved at its front end.

The light-emitting elements (12) are arranged in this embodiment in a flat holding plate (19) in such a way that their optical axes cut one another in a region of focus (20) which lies at the entrance end of the light-absorbing unit (18) that is located inside the housing (10) and provided with an antireflection coating.

The angle, increasing with the distance from the central axis, by which the optical axis of each light-emitting element (12) is tilted, is selected taking account of the light cone aperture and of the distance from the rigid optical fiber rod (18) such that the entire radiation beam of the light-emitting elements (12) falls substantially onto the entrance surface of the rigid optical fiber rod (18) and illuminates the latter essentially completely. In order also to be able to use the light impinging on the light entrance surface for the irradiation of he treatment site, it must be launched into the optical conductor. Consequently, the angle at which the beams strike the entrance surface may not be greater than the maximum acceptance angle of the rigid optical fiber rod. This limits the number of light-emitting elements that can be sensibly integrated in the arrangement shown. When the distance of the light-emitting elements from the entrance surface in conjunction in this case with the narrowest possible angle of emission of he light-emitting elements is selected such that the optical conductor is illuminated as completely as possible and in addition, as far as possible no light is shone past said optical conductor, there is an optimum in the number of elements. Angles of emission in the range of approximately +/−15° of the light-emitting elements have proved themselves, in particular, in the case of this exemplary embodiment.

Instead of the above described planar arrangement, the light-emitting elements can also be arranged on a curved, in particular surface that is concave toward the region of focus. This has the advantage that the distances of the light-emitting elements from the optical conductor are then identical, which cannot be exactly achieved in the case of a flat arrangement. The sizes of the illuminating spots which are generated by the individual light cones on the light entrance orifice then correspond even better to the latter.

In each case one of the supply leads of the light-emitting elements (12), preferably the cathode, is thermally connected to a member (21) made from a material of high thermal conductivity and capacity, preferably copper and/or aluminum, which is used as heat sink for the light-emitting diodes (12).

Since in this embodiment the light-emitting elements (12) lie in a common planar or curved plane, the heat sink member (21), which is intended to be arranged for optimum effect as close as possible to the light-emitting elements (12), has the shape in this embodiment of a plane-parallel disk arranged parallel to the holding disk (19). This is favorable from the point of view both of a low outlay on production, and of a compact design.

Figure 3:
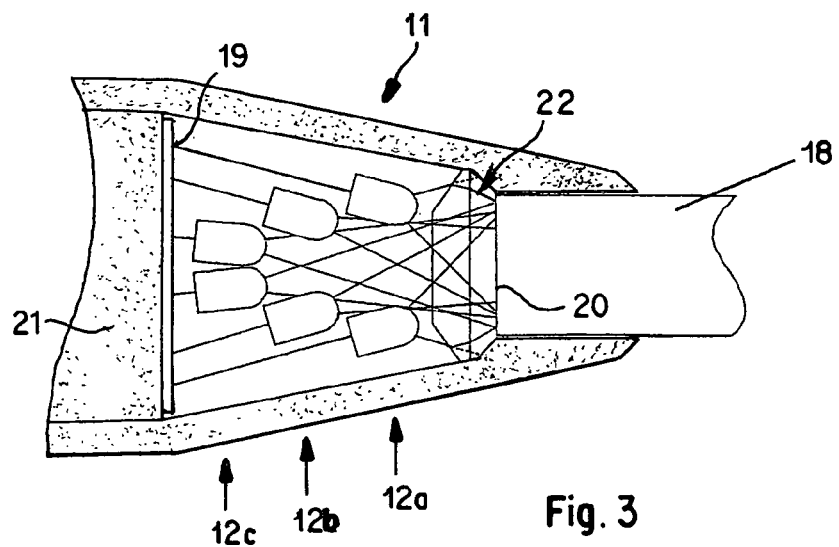
FIG. 3 shows a further embodiment of he front region of the irradiation unit.

FIG. 3 shows a further embodiment of the front region of the irradiation unit in cross section with a light-emitting unit (11), a light-absorbing unit (18), and a plurality of light-emitting elements (12) that are arranged (12a, 12b, 12c) on three planes, the aperture angle of the light elements of the first plane (12a), which is arranged closest to the entrance orifice, being greater than the aperture angle of the light-emitting elements of the second (12b) and third plane (12c), that are arranged further removed from the entrance orifice.

The light-emitting elements of the first and second planes are arranged on an annular surface, while the light-emitting elements of the third plane are located on a circular surface. Also indicated is the degree, differing depending on the plane, by which the light-emitting elements are tilted toward the center of the ring. This ensures that the light cones of the second and third planes firstly can shine past the light-emitting elements of the planes in front, but that secondly, they strike the light entrance orifice and illuminate the latter completely.

In the exemplary embodiment shown, there is located between the light-emitting unit (11) and light-absorbing unit (18) a prismatic disk (22) that, in its edge region, refract toward the entrance orifice the light radiated by the light-emitting elements of the first plane (12a) laterally past the entrance orifice of the light-absorbing unit. It is also possible, in particular, for the diameter of the first plane to be enlarged with the aid of the prismatic disk. Consequently, on the one hand a larger number of light-emitting elements finds room on this ring, and on the other hand the circular opening in the center of this plane is enlarged, as a result of which a larger number of light-emitting elements can also be accommodated in the downstream planes. The planar central region, whose diameter corresponds approximately to the diameter of the light entrance orifice, ensures that the latter can be directly irradiated as before, that is to say the direction of the beams directed onto it is not deflected. However, with the aid of the prismatic edge region additional radiation is directed onto the optical conductor and thereby further raises the light power of the unit.

In the exemplary embodiment shown, all the light-emitting elements are mounted on a holding plate (19) at which there is located on the under side a heat sink (21) in the form of a copper member.

The exposure unit according to the invention is applied particularly in the field of medicine preferably in dentistry, and can serve, on the one hand, for illuminating the treatment site or for irradiating compounds that can be hardened by light, in particular dental filling materials such as composites, compomers or glass ionomer cements.

During use, the exit end of the rigid optical fiber rod is directed onto the treatment site, for example a tooth filling to be hardened, and the closing push-button is pressed, as a result of which the light-emitting diodes are activated and the display unit is simultaneously switched on. After a prescribed or settable time interval, the control circuit switches off the power supply to the light-emitting diodes and the display unit.

LIST OF REFERENCE NUMERALS

10 Housing
11 Light-emitting unit/array
12 Light-emitting elements/light-emitting diodes
13 Battery
14 Driver stage
15 Control circuit
16 Closing push-button
17 Display unit
18 Light-absorbing unit optical fiber rod
19 Holding plate
20 Region of focus
21 Heat sink member
22 Prismatic disk

What is claimed is:

1. An irradiation unit comprising a light-emitting unit contained within a housing, and a light-conducting unit having an entrance aperture,
   the light-emitting unit comprising a plurality of light-emitting elements each of which has a light cone, an aperture and an optical axis, and emits a light beam which is directed onto and directly illuminates the entrance aperture,
   wherein each of the light-emitting elements is mounted a distance away from the entrance aperture with an angle of inclination relative to the optical axis,
   wherein the light-emitting elements are arranged on at least two planes parallel to the entrance aperture, a plane furthest removed from the entrance aperture being a circular surface and all other planes being an annular surface having an annular opening, and the light beams emitted by light-emitting elements on a plane further from the entrance aperture illuminate the entrance aperture through the annular opening of the annular surfaces closer to the entrance aperture,
   wherein the light-emitting elements are thermally connected to the housing,
   and wherein the aperture, the distance and the angle of inclination are selected such that the light beam illuminates an area that corresponds substantially to the surface of the entrance aperture.

2. The irradiation unit as claimed in claim 1, in which the light-emitting elements are arranged on three planes.

3. An irradiation unit as claimed in claim 1, where the outer diameter of the plane situated closest to the entrance aperture, measured at the tip of the light-emitting elements, corresponds substantially to the diameter of the entrance aperture.

4. An irradiation unit as claimed in claim 1, wherein the diameter of the opening ring formed by annularly arranged light-emitting elements is greater than the diameter of the circular surface of the plane situated furthest removed from the entrance aperture.

5. An irradiation unit as claimed in claim 1, wherein the distance between the individual planes corresponds substantially to the length of a light-emitting element.

6. An irradiation unit as claimed in claim 1, wherein the light-emitting element on the at least two planes have different angles of inclination.

7. An irradiation unit as claimed in claim 1, wherein the angle of inclination of the light-emitting elements on the plane situated closest to the entrance aperture is greater than the angle of inclination of the light elements of all other planes situated further removed from the entrance aperture.

8. An irradiation unit as claimed in claim 1, wherein the annularly arranged light-emitting elements are tilted toward the center of the ring by an angle in the range from 10° to 30°.

9. An irradiation unit as claimed in claim 1, wherein the light-emitting elements each has an anode and a cathode, wherein the holder is a circuit board having a top side and a rear side and both sides being coated, and wherein the anode is contacted to the top side, and the cathode is contacted to the rear side.

10. An irradiation unit as claimed in claim 1, wherein the light-conducting unit is a rigid optical fiber rod or a flexible optical conductor.

11. An irradiation unit as claimed in claim 1, further comprising a prismatic disk located between the light-emitting unit and the light-conducting unit.

12. An irradiation unit as claimed in claim 11, wherein the prismatic disk has the shape of a flat conical frustum whose smaller diameter corresponds substantially to the diameter of the entrance aperture.

13. An irradiation unit as claimed in claim 11, wherein the smaller side of the prismatic disk faces the light-emitting unit.

14. An irradiation unit as claimed in claim 1, wherein the diameter of the entrance aperture is in the range from 8 to 14 mm, and 8 to 15 light-emitting elements are located on a first plane closest to the entrance aperture.

15. An irradiation unit as claimed in claim 14, wherein 5 to 12 light-emitting elements are located on a second plane next to the first plane.

16. An irradiation unit as claimed in claim 15, wherein 1 to 7 light-emitting elements are located on a third plane next to the second plane.

17. An apparatus for hardening dental filling materials, comprising an irradiation unit of claim 1, and a suitable control unit for controlling voltage and current for the light-emitting elements.

18. A method for hardening dental filling materials, comprising irradiating the dental filling materials using the irradiation unit of claim 1.

19. The method of claim 18, wherein the dental filling material is hardened in situ.

20. An irradiation unit, comprising a light-emitting unit, a housing, and a light-conducting unit having an entrance aperture, wherein the light-emitting unit is contained within the housing, the light-emitting unit comprising a plurality of light-emitting elements each of which has a light cone, an aperture and an optical axis, and emits a light beam which is directed onto and directly illuminates the entrance aperture, wherein the light-emitting element is mounted a distance away from the entrance aperture with an angle of inclination relative to the optical axis, wherein the light-emitting elements are thermally connected to the housing, wherein the light-emitting elements are arranged with different angles of inclination in a substantially planar holder, and wherein the aperture, the distance and the angle of inclination are selected such that the light beam illuminates an area that corresponds substantially to the surface of the entrance aperture.

21. An irradiation unit, comprising a light-emitting unit, and a light-conducting unit having an entrance aperture, the light-emitting unit comprising a plurality of light-emitting elements each of which has a light cone, an aperture and an optical axis, and emits a light beam which is directed onto and directly illuminates the entrance aperture, wherein each of the light-emitting elements is mounted a distance away from the entrance aperture with an angle of inclination relative to the optical axis, wherein the light-emitting elements are arranged on at least two planes parallel to the entrance aperture, a plane furthest removed from the entrance aperture being a circular surface and all other planes being an annular surface having an annular opening, and the light beams emitted by light-emitting elements on a plane further from the entrance aperture illuminate the entrance aperture through the annular opening of the annular surfaces closer to the entrance aperture, wherein the at least two planes are separated by a distance that corresponds essentially to the length of the light-emitting elements, and wherein the aperture, the distance and the angle of inclination are selected such that the light beam illuminates an area that corresponds substantially to the surface of the entrance aperture.

* * * * *

UNITED STATES PATENT AND TRADEMARK OFFICE
CERTIFICATE OF CORRECTION

PATENT NO. : 6,932,599 B1
DATED : August 23, 2005
INVENTOR(S) : Hartung, Martin G.

It is certified that error appears in the above-identified patent and that said Letters Patent is hereby corrected as shown below:

Title page,
Item [56], References Cited, FOREIGN PATENT DOCUMENTS, below "97/36552" delete "WO     9736552     10/1997"; below "99/16136" delete "WO    9916136     4/1999"; below "99/35995" delete "WO    9935995     7/1999"; and below "00/13608" delete "WO    0013608     3/2000".

Column 1,
Line 14, delete "he" and insert -- the --.

Column 2,
Line 23, after "99/35995" delete "9".

Column 3,
Line 49, delete "tot he" and insert -- to the --.

Column 5,
Line 6, delete "he" and insert -- the --.
Line 57, delete "NIMH" and insert -- NiMH --.

Column 6,
Lines 3, 20, 40 and 48, delete "he" and insert -- the --.

Signed and Sealed this

Twenty-eighth Day of February, 2006

JON W. DUDAS
*Director of the United States Patent and Trademark Office*